United States Patent
Lamb et al.

(10) Patent No.: US 9,223,903 B2
(45) Date of Patent: Dec. 29, 2015

(54) ANALYZING DATA FROM A SENSOR-ENABLED DEVICE

(75) Inventors: John P. Lamb, White Plaines, NY (US); Henry C. Will, IV, Dover, NJ (US)

(73) Assignee: International Business Machines Corporation, Armonk, NY (US)

( * ) Notice: Subject to any disclaimer, the term of this patent is extended or adjusted under 35 U.S.C. 154(b) by 181 days.

(21) Appl. No.: 13/450,540

(22) Filed: Apr. 19, 2012

(65) Prior Publication Data

US 2013/0282695 A1    Oct. 24, 2013

(51) Int. Cl.
G06F 17/30 (2006.01)
A46B 15/00 (2006.01)
G06F 19/00 (2011.01)

(52) U.S. Cl.
CPC ...... *G06F 17/30991* (2013.01); *A46B 15/0002* (2013.01); *A46B 15/0004* (2013.01); *A46B 15/0006* (2013.01); *A46B 15/0008* (2013.01); *A46B 15/0012* (2013.01); *G06F 19/3418* (2013.01)

(58) Field of Classification Search
CPC ......... G06F 19/30; G06F 19/32; G06F 19/34; G06F 19/3406; G06F 19/3418; G06F 19/3487; G06F 17/30991; A46B 15/0002; A46B 15/0008; A46B 15/0004; A46B 15/0006; A46B 15/0012
See application file for complete search history.

(56) References Cited

U.S. PATENT DOCUMENTS

| 4,716,614 | A  | * | 1/1988  | Jones et al. ............ 15/105 |
| 5,561,881 | A  |   | 10/1996 | Klinger et al. |
| 6,687,695 | B1 |   | 2/2004  | Miller et al. |
| 6,786,732 | B2 |   | 9/2004  | Savill et al. |
| 6,816,848 | B1 |   | 11/2004 | Hildreth et al. |
| 6,839,753 | B2 | * | 1/2005  | Biondi et al. ............ 709/224 |
| 7,748,069 | B2 | * | 7/2010  | Dawley ................... 15/22.1 |
| 7,946,845 | B2 |   | 5/2011  | Lehmann |

(Continued)

FOREIGN PATENT DOCUMENTS

| JP | 2011-156204 | * | 8/2011 | ............... A61C 1/07 |
| WO | WO2012020165 A1 | * | 2/2012 | ............. A46B 15/00 |

OTHER PUBLICATIONS

"Is Cloud the tomorrow of Medical Devices Industry?" by Dutta, Arindam. (Jan. 3, 2011). Available at: http://www.hcltech.com/blogs/engineering-and-rd-services/cloud-tomorrow-medical-devices-industry.*

(Continued)

*Primary Examiner* — Daniel Kinsaul
(74) *Attorney, Agent, or Firm* — Noah A. Sharkan; Maxine L. Barasch; Keohane & D'Alessandro PLLC (57) ABSTRACT

An approach for analyzing data collected by a sensor-enabled device over a network is provided. Specifically, in a typical embodiment, a set of usage data will be received from a device over a network. The set of usage data may be collected via at least one sensor integrated with the device, and the set of usage data may pertain to use of the device by a user. Regardless, the set of usage data will be compared to a set of diagnostic information stored in at least one computer storage device. The set of diagnostic information typically pertains to a condition (e.g., medical) treated by use of the device (e.g., dental, cardiac, renal, etc.). Based on the comparison, at least one determination (e.g., diagnosis, treatment plan, level of compliance with applicable standards, etc.) will be made and a set of reports will be generated based thereon.

25 Claims, 4 Drawing Sheets

(56) References Cited

U.S. PATENT DOCUMENTS

| | | | |
|---|---|---|---|
| 8,308,651 B1* | 11/2012 | Baruti | 600/538 |
| 2002/0183959 A1 | 12/2002 | Savill et al. | |
| 2005/0234352 A1* | 10/2005 | Bardy | 600/508 |
| 2005/0283210 A1* | 12/2005 | Blischak et al. | 607/60 |
| 2006/0031094 A1* | 2/2006 | Cohen et al. | 705/2 |
| 2007/0190509 A1* | 8/2007 | Kim | 434/263 |
| 2008/0060148 A1 | 3/2008 | Pinyayev et al. | |
| 2009/0130636 A1* | 5/2009 | Hwang | 433/216 |
| 2009/0177769 A1* | 7/2009 | Roberts | 709/224 |
| 2009/0215015 A1 | 8/2009 | Chu | |
| 2009/0291422 A1 | 11/2009 | Puurunen et al. | |
| 2009/0307859 A1 | 12/2009 | Mottram et al. | |
| 2009/0317770 A1* | 12/2009 | Gatzemeyer et al. | 433/215 |
| 2010/0175208 A1* | 7/2010 | Hilfinger et al. | 15/22.1 |
| 2010/0281636 A1* | 11/2010 | Ortins et al. | 15/4 |
| 2011/0033833 A1* | 2/2011 | Blomquist et al. | 434/262 |
| 2012/0179908 A1* | 7/2012 | Duma | 713/165 |
| 2012/0295216 A1* | 11/2012 | Dykes et al. | 433/27 |
| 2013/0333126 A1* | 12/2013 | Miller | 15/22.1 |

OTHER PUBLICATIONS

"Sensor Network for Medical Care," by Shnayder et al. In: Tech. Report TR-08-05, Harvard Univ. (2005). Available at: http://www.eecs.harvard.edu/~konrad/papers/codeblue-techrept05.pdf.*

Maitland, J., "Keeping Control Isn't Easy", Chapter 4: Cloud-Based Infrastructure, SearchCloudComputing.com, 13 pages.

Mell et al., "The NIST Definition of Cloud Computing", National Institute of Standards and Technology, Information Technology Laboratory, Version 15, Oct. 7, 2009, 2 pages.

Chang, Y.C. et al., "Playful Toothbrush: UbiComp Technology for Teaching Tooth Brushing to Kindergarten Children", CHI 2008, Apr. 5-10, 2008, Florence, Italy, 10 pages.

"Ecran Smart Guide", Oral-B Professional Care Smart Series 5000, 31 pages. No authors cited. Publication date not cited.

"IBM; Made in IBM Labs: IBM Reinvents the Patient Portal", w3.ibm.com, Mar. 15, 2011, 3 pages. No authors cited.

"Social Commerce", IBM Social Commerce Global Summit 2011, 4 pages. http://www-01.ibm.com/software/genservers/commerce/socialcommerce/. No authors cited. Publication date not cited.

"Made in IBM Labs: IBM Reinvents the Patient Portal", IBM News room, Mar. 3, 2011, 3 pages. http://www-03.ibm.com/press/us/en/pressrelease/33944.wss.

"Customer relationship management solutions", IBM and Alliance. http:/www.ibm.com/solutions/alliance/us/en/index/crm.html.

"Smarter by the second", www.ibm.com, 3 pages. No authors cited. Publication date.

Barras, C., "Computerised toothbrush makes oral hygiene a game", NewScientist, Apr. 4, 2008, 2 pages.http://www.newscientist.com/article/dnl35998-computerised-toothbrush-....

"Made in IBM Labs: IBM Reinvents the Patient Portal", www-03.ibm.com, Mar. 3, 2011, 3 pages. No authors cited.

"Brush Smart!", Beam Technologies, 1 page. http://Beamtoothbrush.com/beam/brush-overview.php.

Maitland, J., "Keeping Control Isn't Easy", Chapter 4: Cloud-Based Infrastructure, SearchCloudComputing.com, Publication Date: Oct. 2009, 19 pages.

"Ecran Smart Guide", Oral-B Professional Care Smart Series 5000, May 26, 2010, 31 pages.

"Customer relationship management solutions", IBM and Alliance. http:/www.ibm.com/solutions/alliance/us/en/index/crm.html, Mar. 4, 2012, 2 pages.

"Smarter by the second", Smarter Planet—Analytics—Solutions, www.ibm.com, Mar. 4, 2012, 3 pages.

"Brush Smart!", Beam Technologies, 1 page. http://Beamtoothbrush.com/beam/brush-overview.php, Apr. 10, 2012.

* cited by examiner

ANALYZING DATA FROM A SENSOR-ENABLED DEVICE

TECHNICAL FIELD

In general, embodiments of the present invention relate to data analysis. Specifically, embodiments of the present invention relate to the analysis of data from a sensor-enabled device (e.g., a medical device) over a network (e.g., a cloud computing network).

BACKGROUND OF THE INVENTION

As technology continues to advance, medical devices/processes continue to evolve. For example, many medical devices and/or medical implements may be used to capture various forms of data. Such data may be used by a medical professional to diagnosis and/or treat a patient.

Challenges may exist where a healthcare provider and/or specialist is not co-located with the medical device or the patient. Moreover, a typical healthcare care provider may analyze information recorded by such devices based on his/her own immediate knowledge or whatever references are available. As such, valuable time may be lost and/or an incomplete analysis may be performed.

SUMMARY

In general, embodiments of the present invention provide an approach for analyzing data collected by a sensor-enabled device (e.g., a medical device/implement) over a network (e.g., a cloud computing network). Specifically, in a typical embodiment, a set of usage data will be received from a device over a network. The set of usage data may be collected via at least one sensor integrated with the device, and the set of usage data may pertain to use of the device by a user. Regardless, the set of usage data will be compared to a set of diagnostic information stored in at least one computer storage device. The set of diagnostic information typically pertains to a condition (e.g., medical) treated by use of the device (e.g., dental, cardiac, renal, etc.). Based on the comparison, at least one determination (e.g., diagnosis, treatment plan, level of compliance with applicable standards, etc.) will be made and a set of reports will be generated based thereon.

A first aspect of the present invention provides a computer-implemented method for analyzing data from a sensor-enabled device, comprising: receiving a set of usage data from the device over a network, the set of data being collected via at least one sensor integrated with the device, and the set of data pertaining to use of the device by a user; comparing the set of usage data to a set of diagnostic information stored in at least one computer storage device, the set of diagnostic information pertaining to a condition treated by use of the device; making at least one determination based on the comparing; and generating a set of reports based on the at least one determination.

A second aspect of the present invention provides a system for analyzing data from a sensor-enabled device, comprising: a memory medium comprising instructions; a bus coupled to the memory medium; and a processor coupled to the bus that when executing the instructions causes the system to: receive a set of usage data from the device over a network, the set of usage data being collected via at least one sensor integrated with the device, and the set of usage data pertaining to use of the device by a user; compare the set of usage data to a set of diagnostic information stored in at least one computer storage device, the set of diagnostic information pertaining to a condition treated by use of the device; make at least one determination based on the comparison; and generate a set of reports based on the at least one determination.

A third aspect of the present invention provides a computer program product for analyzing data from a sensor-enabled device, the computer program product comprising a computer readable storage media, and program instructions stored on the computer readable storage media, to: receive a set of usage data from the device over a network, the set of usage data being collected via at least one sensor integrated with the device, and the set of usage data pertaining to use of the device by a user; compare the set of usage data to a set of diagnostic information stored in at least one computer storage device, the set of diagnostic information pertaining to a condition treated by use of the device; make at least one determination based on the comparison; and generate a set of reports based on the at least one determination.

A fourth aspect of the present invention provides a method for deploying a system for analyzing data from a sensor-enabled device, comprising: providing a computer infrastructure being operable to: receive a set of usage data from the device over a network, the set of usage data being collected via at least one sensor integrated with the device, and the set of usage data pertaining to use of the device by a user; compare the set of usage data to a set of diagnostic information stored in at least one computer storage device, the set of diagnostic information pertaining to a condition treated by use of the device; make at least one determination based on the comparison; and generate a set of reports based on the at least one determination.

BRIEF DESCRIPTION OF THE DRAWINGS

These and other features of this invention will be more readily understood from the following detailed description of the various aspects of the invention taken in conjunction with the accompanying drawings in which.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

Illustrative embodiments will now be described more fully herein with reference to the accompanying drawings, in which exemplary embodiments are shown. This disclosure may, however, be embodied in many different forms and should not be construed as limited to the exemplary embodiments set forth herein. Rather, these exemplary embodiments are provided so that this disclosure will be thorough and complete and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The word "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

As mentioned above, embodiments of the present invention provide an approach for analyzing data collected by a sensor-enabled device (e.g., a medical device/implement) over a network (e.g., a cloud computing network). Specifically, in a typical embodiment, a set of usage data will be received from a device over a network. The set of usage data may be collected via at least one sensor integrated with the device, and the set of usage data may pertain to use of the device by a user. Regardless, the set of usage data will be compared to a set of diagnostic information stored in at least one computer storage device. The set of diagnostic information typically pertains to a condition (e.g., medical) treated by use of the device (e.g., dental, cardiac, renal, etc.). Based on the comparison, at least one determination (e.g., diagnosis, treatment plan, level of compliance with applicable standards, etc.) will be made and a set of reports will be generated based thereon.

Figure 1:
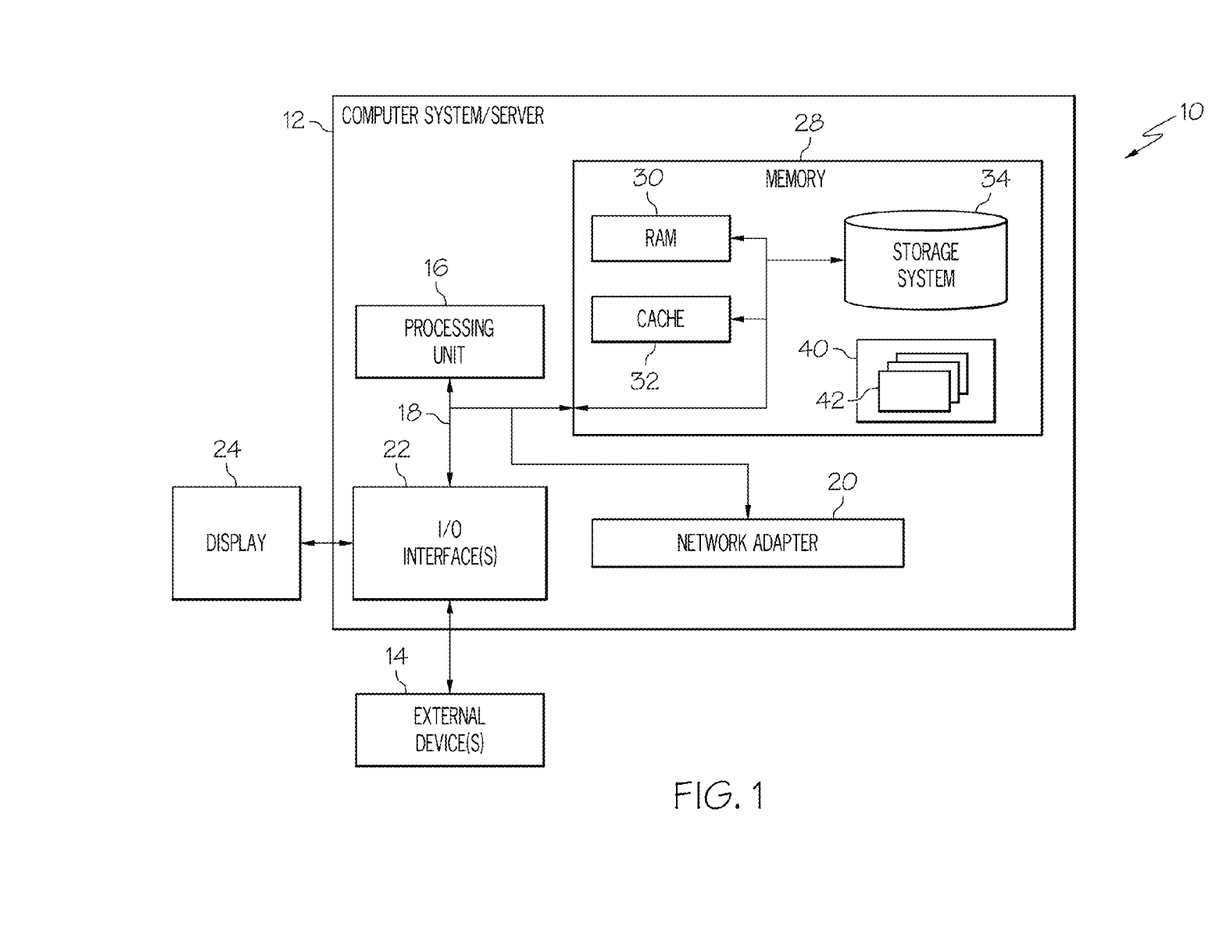
FIG. 1 depicts a computing node according to an embodiment of the present invention.

Referring now to FIG. 1, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10, there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, mobile devices, global positioning systems (GPS), GPS-enabled devices, multiprocessor systems, microprocessor-based systems, set top boxes, programmable consumer electronics, network PCs, minicomputer systems, mainframe computer systems, and distributed computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on, that perform particular tasks or implement particular abstract data types. Computer system/server 12 may be practiced in distributed computing environments where tasks are performed by remote processing devices that are linked through a communications network. In a distributed computing environment, program modules may be located in both local and remote computer system storage media including memory storage devices.

As shown in FIG. 1, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

The embodiments of the invention may be implemented as a computer readable signal medium, which may include a propagated data signal with computer readable program code embodied therein (e.g., in baseband or as part of a carrier wave). Such a propagated signal may take any of a variety of forms including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium including, but not limited to, wireless, wireline, optical fiber cable, radio-frequency (RF), etc., or any suitable combination of the foregoing.

Data analysis program/utility 40, having a set (at least one) of program modules 42, may be stored in memory 28 by way of example, and not limitation, as well as an operating system, one or more application programs, other program modules, and program data. In general, data analysis program/utility 40 performs the function of the present invention as described herein. Each of the operating systems, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), a cloud computing network, and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
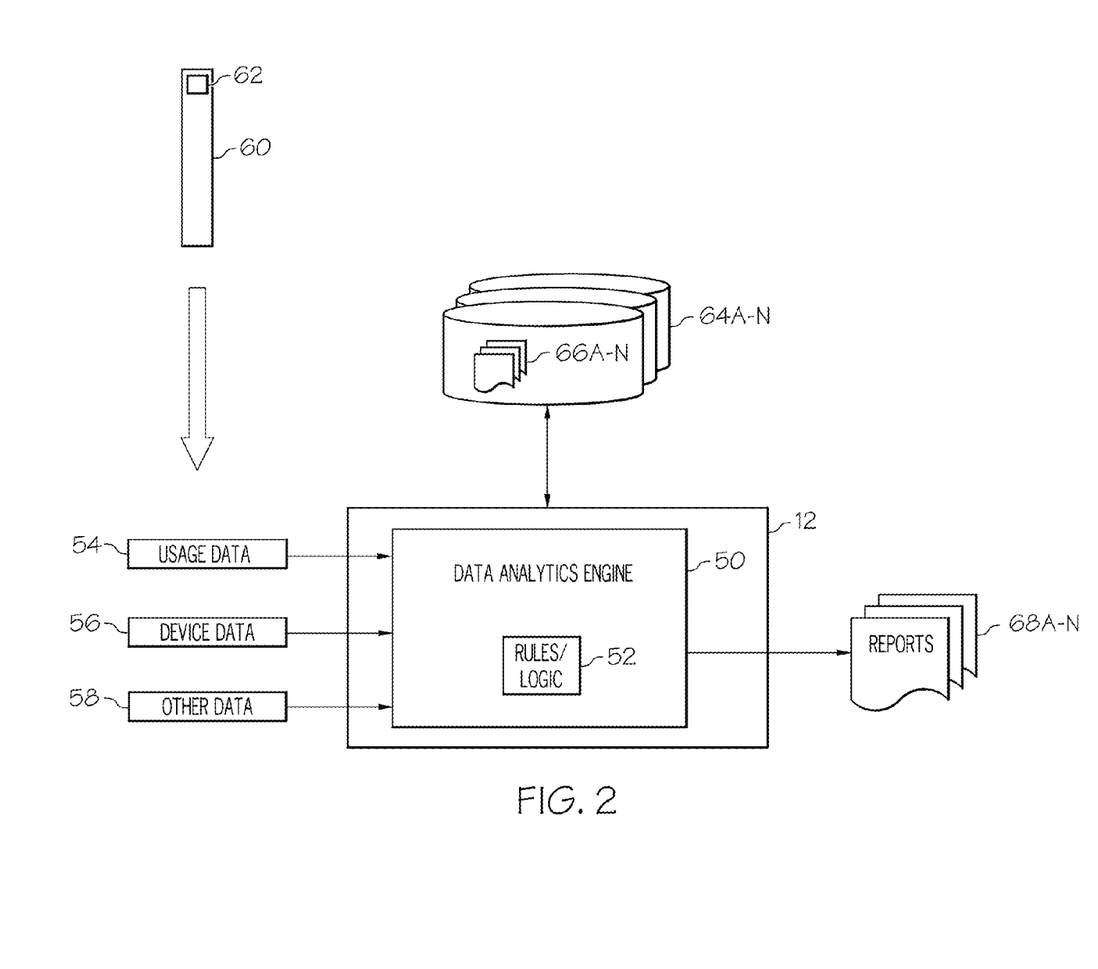
FIG. 2 depicts a system diagram according to an embodiment of the present invention.

Referring now to FIG. 2, a system diagram describing the functionality discussed herein according to an embodiment of the present invention is shown. It is understood that the teachings recited herein may be practiced within any type of networked computing environment (e.g., a cloud computing environment). A computer system/server 12, which can be implemented as either a stand-alone computer system or as a network computer system is shown in FIG. 2. In the event the teachings recited herein are practiced in a networked computing environment, each client need not have a data analytics engine (engine 50). Rather, engine 50 could be loaded on a server or server-capable device that communicates (e.g., wirelessly) with the clients to provide data analysis functionality hereunder. Regardless, as depicted, engine 50 is shown within computer system/server 12. In general, engine 50 can be implemented as data analysis program/utility 40 on computer system 12 of FIG. 1 and can enable the functions recited herein. As further shown, engine 50 (in one embodiment) comprises a rules and/or computational engine that processes a set (at least one) of rules/logic 52 and/or provides data analysis functionality hereunder.

As indicated above, embodiments of the present invention are based on an application and algorithm that may analyze information received from device sensors to determine the efficiency and/or effectiveness of a user's operation of the device. It is understood that although an illustrative embodiment discussed herein pertains to toothbrushes and dental hygiene, the teachings recited herein could be applied to any type of device in any type of field (e.g., medical field) such as a glucose monitor, a hair brush, a heart rate monitor, dialysis equipment, etc. As such, it is understood that the teachings recited herein are not intended to be limited to dental hygiene analysis.

Along these lines, engine 50 may perform multiple functions similar to a general-purpose computer. Specifically, among other functions, engine 50 may (among other things): receive (e.g., from a device 60 and/or manufacturer of device 60) a set of usage data 54, device data 56 (e.g., device type, product specifications, etc.), and/or other data 58 (e.g., material information etc.) over a network (e.g., a cloud computing network), the set of usage data 54 being collected via at least one sensor 62 integrated with the device 60, and the set of usage data 54 pertaining to use of the device 60 by a user (e.g., a patient, a medical practitioner using device 60, etc.); compare the set of usage data 54 to a set of diagnostic information 66A-N stored in at least one computer storage device 64A-N, the set of diagnostic information 66A-N pertaining to a condition (e.g., a medical state) treated by use of the device 60; make at least one determination (e.g., a medical condition of the user, such as a level of effectiveness of use of device 60) based on the comparison (and device data 56 and/or other data 58); and generate a set of reports 68A-N based on the at least one determination.

In an illustrative dental embodiment, device 60 may be a tooth brush and usage data 54 may pertain to a user's use of the toothbrush. This information/data may be aggregated (e.g., by engine 50) along with diagnostic information 66A-N (e.g., cavity data) received from a healthcare provider and/or knowledge database, device data 56 (toothbrush's specifications) received from a manufacturer or the like of the toothbrush, and/or other data 58 (e.g., toothpaste type) received from a toothpaste manufacturer to determine the best toothpaste and brushing habits to reduce tooth decay. Such data aggregation may allow for evaluation of types of brush designs (speed, length of brush heads, depth of brushes, battery life, types of materials for effectiveness and longevity), toothpastes, effectiveness of different brushing techniques, etc.

This data may be aggregated and sent to a dental practitioner where it could be used to analyze where cavities occur compared to brushing techniques. For example, the data may reveal that up and down brushing on some teeth surfaces work better for certain users, while a back and forth technique works better for other users. Moreover, the data may reveal that certain toothpastes need more or less brushing time, caused extra tooth wear, etc. Still yet, this data may indicate how the user's brushing techniques affected his/her gum recession.

Figure 3:
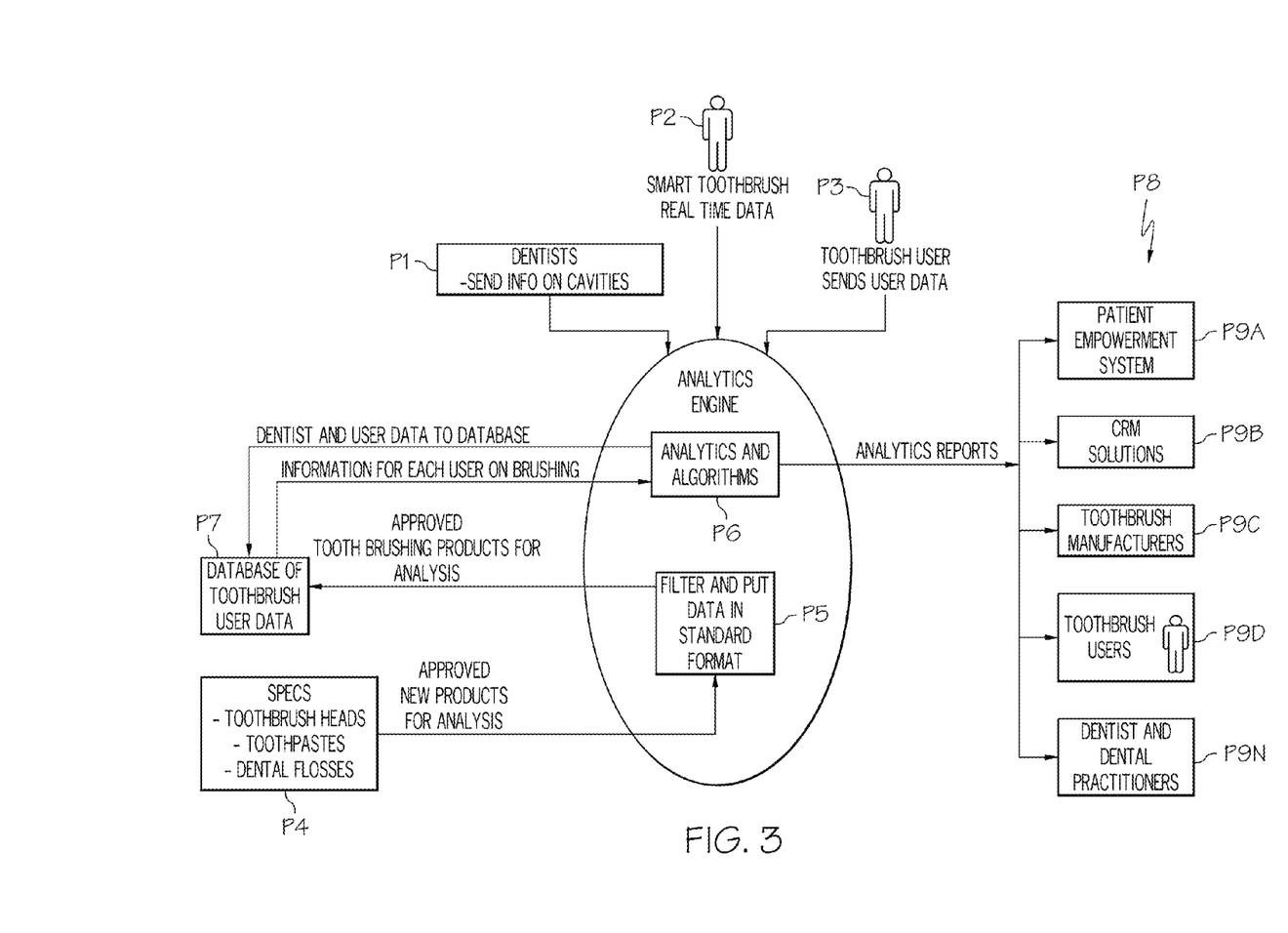
FIG. 3 depicts a system flow diagram according to an embodiment of the present invention.

FIG. 3 shows an example of a process/system flow diagram evaluation of data from smart toothbrushes. It is understood that similar teachings could be applied to other field/types of devices (e.g., renal, cardiothoracic, etc.), a dental example is depicted and described for ease of illustration and simplicity purposes. As indicated in the diagram, this approach may provide dentists, toothbrush users, toothbrush manufacturers, dental practitioners, toothpaste and floss manufacturers, etc., with the analytics reports required to significantly improve tooth brushing. For example, this approach may be used to improve: tooth brush design (e.g., battery life, layout of bristles, mechanical brushing capabilities); methods of brushing (e.g., time of day, length of time brushing, frequency of brushing, amount of pressure used, etc.); and/or toothpaste design (e.g., amount of grit, whitening agents, decay prevention, plaque prevention, etc.).

As shown in FIG. 3, various forms of information/data may be collected hereunder. In step P1, data may be collected from a dental provider. Such data may comprise: cavity information (e.g., tooth position and surface); root canal information (e.g., tooth and surface); gum recession information; tooth sensitivity information; whiteness measurement information, etc. In step P2, data may be collected from the sensor-enabled toothbrush. Such data may comprise: brush position (e.g., tooth and surface, angle, etc.); brushing pressure; length of brushing time; battery charge time; battery current charge amount/level; type of brush head installed and when installed (e.g., engine 50 could determine an optimal time to change head); unique unit design identification (e.g., for brush and mechanism design parameters, such as speed, rotary, or back and forth, etc. to be accessed). In step P3, data may be collected from a user of the toothbrush. Such data may comprise: the type of toothpaste being used (e.g., received a scan, or other input such as separate input via a cloud application or the like); times of eating; types of food eaten; flossing times and amount; type of flossing used (string or tape or toothpick, etc.); whether the user is right-handed or left-handed, etc. Still yet, as shown in step P4, data may be collected from the toothbrush and/or toothpaste manufacturer(s). Such data may comprise: information pertaining to a design of the brush head (e.g., bristle material, size of bristles, length of bristles, number of bristles, angle of bristle cut, etc.); and information pertaining to the design of the mechanism (e.g., battery, type of brushing: rotary or back and forth, etc.); information pertaining to any toothpaste whitening agents present; fluoride types and other decay prevention agents; amount of toothpaste grit; plaque prevention agent(s) present; etc. It is understood that since the data collected in step P4 may be collected from a variety of sources, such data may be filtered and/or placed into a standard data format P5 that is recognizable/usable by the system. Regardless, once some or all of this data has been collected (and filtered/standardized), such data may be processed and analyzed in step P6, and potentially stored in step P7, so as to determine a user's dental progress and or hygiene. A set of reports may then be generated in step P8. As shown, such reports may be provided to a variety of recipients such as patient empowerment systems P9A, customer relationship management (CRM) system P9B, toothbrush manufacturers P9C, toothbrush users P9D, dental practitioners P9N, etc.

Illustrative Use Cases

Shown hereinbelow are illustrative use cases describing embodiments in which the teachings recited above may be utilized. It is understood that the embodiments of the present invention are not intended to be limited to these use cases.

Example—Use Case 1

Utilization of Toothbrush Usage Compared to Cavity Outcomes

Overview: Assume in this example that a dentist, who has several patients with sensor-enabled toothbrushes, sends tooth health information to the system and the patient's toothbrushes send information on brushing habits. The engine then combines and analyzes the brushing habit information with the tooth health information to determine how brushing habits affect teeth health. Under such a scenario, the following steps may be performed:

1. Dentist submits information to system (e.g., cavity information such as tooth position, surface, etc.);
2. The dentist's patients' sensor enabled tooth brushes provide the following information on usage: position (tooth and surface, angle), pressure and length of time on each tooth surface, etc.;
3. Analytics are performed based on information received. Specifically, the analytics engine may compare the average time and pressure spent on each tooth surface to the average number of cavities on a per user basis to determine the optimal brushing pressure and length of time per tooth to maximize tooth health; and
4. An analytics report is sent to the dentist.

Example Use Case 2

Cavity Reduction Program with Dentist Based on Recommendation Data from Aggregated Tooth Brushing Studies Assume in this example that a patient wishes to participate in a study/program. Under such a scenario, the following steps may be performed:

1. A patient decides to enroll in a toothpaste/toothbrush program;
2. A dentist sends information regarding the patient's cavities (e.g., location and other related data), whiteness factors, enamel factors, etc., to the analytics engine;
3. The engine matches the patient's data to highest aggregate percentages of other patients in a database;
4. The engine analyzes these matched records to find the most effective toothpaste/toothbrush/frequency, pressure, bristle type, etc., for this type of patient;
5. Recommendations are passed back to the patient via the dentist;
6. The sensor-enabled toothbrush may monitor and provide real-time feedback to the patient if they are following the recommendations;
7. Follow up with the dentist by dentist inputting the resulting data from the sensor-enabled toothbrush and any dental exams; and
8. The process may be repeated for follow-up care.

Example Use Case 3

Real Time Analysis and Feedback to Toothbrush User on Pressure and Time Spent on Each Tooth Surface Assume in this example that a user wishes to receive feedback based on his/her use of the sensor-enabled toothbrush and the corresponding system described herein. Under such a scenario, the following steps may be performed:

1. A User initially brushes his/her teeth multiple times;
2. The sensor-enabled toothbrush collects data of time and pressure applied to each tooth surface;
3. After one or more tooth brushing sessions, data is communicated for analysis hereunder;
4. An analysis is made of time and pressure applied to each tooth surface as well as the order of teeth being brushed;
5. Optionally, a graph showing the average, high, and lowest pressure on each tooth may be shown to provide visual feedback to the user;
6. Optionally, a graphical representation of an amount of time spent on each tooth surface may be shown to provide visual feedback to the user;
7. The user brushes his/her teeth; and
8. The sensor-enabled toothbrush provides real-time feedback of the amount of pressure and time applied for each tooth surface. For example, a warning noise and/or vibration may be provided if brushing pressure is too much or too little. Also, once an allotted time is spent on each tooth, there may be additional feedback needed to move to next surface. This warning may increase if too much time is spent on one surface.

Example Use Case 4

Program to Evaluate Best Toothbrush and Toothpaste Design

Assume in this example that toothbrush and/or toothpaste manufacturers wish to participate in a program to evaluate their designs. Under such a scenario the following steps may be performed:

1. Manufacturers of toothbrushes opt into the program;
2. Manufacturers of toothpastes opt into the program;
3. Dentists are asked to participate in and opt into the program;

4. Patients/users are asked to participate in and opt into the program;

5. Dentists perform a full evaluation on each patient (e.g., cavity history, frequency of cavities, tooth whiteness, hardness, plaque buildup, etc.);

6. Patients are assigned a smart toothbrush and toothpaste with multiple aspects: type of mechanical action (e.g., circular motion, rectangular motion, etc.), type of bristles (e.g., bristle thickness, density, angle of cut edge, hardness), type of toothpaste (whiteness, plaque, fluoride concentration, etc.);

7. The patients use the sensor-enabled toothbrushes according to an assigned schedule;

8. The sensor-enabled toothbrushes' records are updated with brushing data pursuant to use of the sensor-enabled toothbrushes;

9. The sensor-enabled toothbrushes upload the data (real-time or batch);

10. The engine analyzes the data and provides feedback to the manufacturers, dentists, and/or patients;

11. At the end of the program, the dentists perform a full dental evaluation on the patients and input corresponding data into a database;

12. The engine evaluates the data; and

13. The engine provides reports on the best types of these features according to patient types (e.g. people with very hard teeth should brush twice a day using y bristle type and x toothpaste type, etc.).

Figure 4:
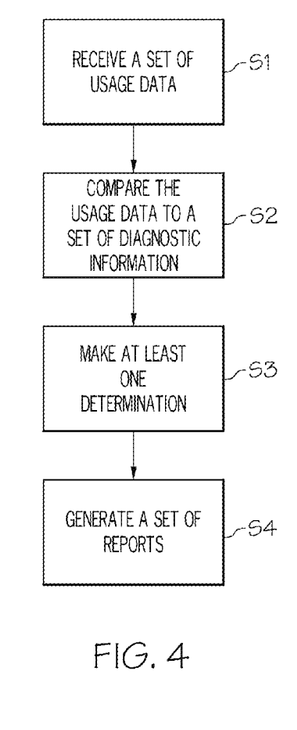
FIG. 4 depicts a method flow diagram according to an embodiment of the present invention.

Referring now to FIG. 4, a method flow diagram according to an embodiment of the present invention is shown (e.g., as enabled by engine 50 of FIG. 2). As depicted, in step S1, a set of usage data is received from a device over a network. As indicated herein, the set of usage data is typically collected via at least one sensor integrated with the device, and the set of usage data typically pertains to use of the device by a user. In step S2, the set of usage data is compared to a set of diagnostic information (e.g., pertaining to a condition treated by use of the device) stored in at least one computer storage device. In step S3, at least one determination is made based on the comparison. In step S4, a set of reports is generated based on the at least one determination.

While shown and described herein as a data analysis solution, it is understood that the invention further provides various alternative embodiments. For example, in one embodiment, the invention provides a computer-readable/useable medium that includes computer program code to enable a computer infrastructure to provide data analysis as discussed herein. To this extent, the computer-readable/useable medium includes program code that implements each of the various processes of the invention. It is understood that the terms computer-readable medium or computer-useable medium comprise one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory 28 (FIG. 1) and/or storage system 34 (FIG. 1) (e.g., a fixed disk, a read-only memory, a random access memory, a cache memory, etc.).

In another embodiment, the invention provides a method that performs the process of the invention on a subscription, advertising, and/or fee basis. That is, a service provider, such as a Solution Integrator, could offer to provide data analysis functionality. In this case, the service provider can create, maintain, support, etc., a computer infrastructure, such as computer system 12 (FIG. 1) that performs the processes of the invention for one or more consumers. In return, the service provider can receive payment from the consumer(s) under a subscription and/or fee agreement and/or the service provider can receive payment from the sale of advertising content to one or more third parties.

In still another embodiment, the invention provides a computer-implemented method for data analysis. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

As used herein, it is understood that the terms "program code" and "computer program code" are synonymous and mean any expression, in any language, code, or notation, of a set of instructions intended to cause a computing device having an information processing capability to perform a particular function either directly or after either or both of the following: (a) conversion to another language, code, or notation; and/or (b) reproduction in a different material form. To this extent, program code can be embodied as one or more of: an application/software program, component software/a library of functions, an operating system, a basic device system/driver for a particular computing device, and the like.

A data processing system suitable for storing and/or executing program code can be provided hereunder and can include at least one processor communicatively coupled, directly or indirectly, to memory elements through a system bus. The memory elements can include, but are not limited to, local memory employed during actual execution of the program code, bulk storage, and cache memories that provide temporary storage of at least some program code in order to reduce the number of times code must be retrieved from bulk storage during execution. Input/output and/or other external devices (including, but not limited to, keyboards, displays, pointing devices, etc.) can be coupled to the system either directly or through intervening device controllers.

Network adapters also may be coupled to the system to enable the data processing system to become coupled to other data processing systems, remote printers, storage devices, and/or the like, through any combination of intervening private or public networks. Illustrative network adapters include, but are not limited to, modems, cable modems, and Ethernet cards.

The foregoing description of various aspects of the invention has been presented for purposes of illustration and description. It is not intended to be exhaustive or to limit the invention to the precise form disclosed and, obviously, many modifications and variations are possible. Such modifications and variations that may be apparent to a person skilled in the art are intended to be included within the scope of the invention as defined by the accompanying claims.

What is claimed is:

1. A computer-implemented method for analyzing data from a sensor-enabled toothbrush, comprising:

receiving a set of usage data, pertaining to a user's use of the toothbrush, from the toothbrush over a cloud network, the set of usage data being collected via at least one sensor integrated with the toothbrush, and the set of usage data comprising: an angle of the toothbrush against at least one tooth of the user, a pressure of the toothbrush against the at least one tooth of the user, a length of time the user brushed the at least one tooth, and an order of brushing of the at least one tooth by the user;

providing a first graph showing average, high, and low pressure applied to each tooth surface;

providing a second graph of an amount of time spent on the each tooth surface;

receiving, over the cloud network, usage data pertaining to other users' use of other toothbrushes;

comparing the set of usage data, pertaining to the user's use of the toothbrush, to a set of diagnostic information stored in at least one computer storage device, the set of diagnostic information pertaining to a condition treated by use of the toothbrush;

aggregating, into aggregated usage data, a result of the comparison with the usage data pertaining to other users' use of other toothbrushes;

analyzing the aggregated usage data;

determining, based on the analysis, a correlation of a characteristic of teeth to a parameter of the toothbrush or use of the toothbrush based on the analyzing;

generating a set of reports based on the comparison, the set of reports indicating at least one recommendation based on the correlation, and the most effective toothpaste and bristle type according to patient phenotype.

2. The computer-implemented method of claim 1, further comprising receiving a set of toothbrush information from a manufacturer of the toothbrush, wherein the set of toothbrush information comprises at least one of: a bristle material, a size of bristles, a length of bristles, a number of bristles, or an angle of bristle cut.

3. The computer-implemented method of claim 2, further comprising analyzing the set of toothbrush information in addition to the aggregated usage data.

4. The computer-implemented method of claim 1, the toothbrush being a medical device, and the condition pertaining to a medical state of the user.

5. The computer-implemented method of claim 1, further comprising determining a medical condition of the user.

6. The computer-implemented method of claim 1, making at least one determination pertaining to at least one of: a level of effectiveness of the toothbrush to treat the condition, and a level of compliance of the user with a set of standards for prevention of a medical condition.

7. The computer-implemented method of claim 1, the network comprising a cloud computing network.

8. The method of claim 1, wherein the characteristic of teeth comprises at least one of: cavities in the teeth, gum recession around the teeth, and hardness of the teeth.

9. A system for analyzing data from a sensor-enabled device, comprising:

a memory medium comprising instructions;

a bus coupled to the memory medium; and a processor coupled to the bus that when executing the instructions causes the system to:

receive a set of usage data, pertaining to a user's use of the toothbrush, from the toothbrush over a cloud network, the set of usage data being collected via at least one sensor integrated with the toothbrush, and the set of usage data comprising: an angle of the toothbrush against at least one tooth of the user, a pressure of the toothbrush against the at least one tooth of the user, a length of time the user brushed the at least one tooth, and an order of brushing of the at least one tooth by the user;

provide a first graph showing average, high, and low pressure applied to each tooth surface;

provide a second graph of an amount of time spent on the each tooth surface;

receive, over the cloud network, usage data pertaining to other users' use of other toothbrushes;

compare the set of usage data, pertaining to the user's use of the toothbrush, to a set of diagnostic information stored in at least one computer storage device, the set of diagnostic information pertaining to a condition treated by use of the toothbrush;

aggregate, into aggregated usage data, a result of the comparison with the usage data pertaining to other users' use of other toothbrushes;

analyze the aggregated usage data;

determine, based on the analysis, a correlation of a characteristic of teeth to a parameter of the toothbrush or use of the toothbrush based on the analyzing;

generate a set of reports based on the comparison, the set of reports indicating at least one recommendation based on the correlation, and the most effective toothpaste and bristle type according to patient phenotype.

10. The system of claim 9, the memory medium further comprising instructions for causing the system to receive a set of toothbrush information from a manufacturer of the toothbrush, wherein the set of toothbrush information comprises at least one of: a bristle material, a size of bristles, a length of bristles, a number of bristles, or an angle of bristle cut.

11. The system of claim 10, the memory medium further comprising instructions to analyze the set of toothbrush information in addition to the aggregated usage data.

12. The system of claim 10, wherein the characteristic of teeth comprises at least one of: cavities in the teeth, gum recession around the teeth, and hardness of the teeth.

13. The system of claim 9, the toothbrush being a medical device, and the condition pertaining to a medical state of the user.

14. The system of claim 9, further comprising determining a medical condition of the user.

15. The system of claim 9, making at least one determination pertaining to at least one of: a level of effectiveness of the toothbrush to treat the condition, and a level of compliance of the user with a set of standards for prevention of a medical condition.

16. The system of claim 9, the network comprising a cloud computing network.

17. A computer program product for analyzing data from a sensor-enabled device, the computer program product comprising a computer readable storage device, and program instructions stored on the computer readable storage device, to:

receive a set of usage data, pertaining to a user's use of the toothbrush, from the toothbrush over a cloud network, the set of usage data being collected via at least one sensor integrated with the toothbrush, and the set of usage data comprising: an angle of the toothbrush against at least one tooth of the user, a pressure of the toothbrush against the at least one tooth of the user, a length of time the user brushed the at least one tooth, and an order of brushing of the at least one tooth by the user;

provide a first graph showing average, high, and low pressure applied to each tooth surface;

provide a second graph of an amount of time spent on the each tooth surface;

receive, over the cloud network, usage data pertaining to other users' use of other toothbrushes;

compare the set of usage data, pertaining to the user's use of the toothbrush, to a set of diagnostic information stored in at least one computer storage device, the set of diagnostic information pertaining to a condition treated by use of the toothbrush;

aggregate, into aggregated usage data, a result of the comparison with the usage data pertaining to other users' use of other toothbrushes;

analyze the aggregated usage data;

determine, based on the analysis, a correlation of a characteristic of teeth to a parameter of the toothbrush or use of the toothbrush based on the analyzing;

generate a set of reports based on the comparison, the set of reports indicating at least one recommendation based on the correlation, and the most effective toothpaste and bristle type according to patient phenotype.

18. The computer program product of claim 17, the computer readable storage device further comprising instructions to receive a set of toothbrush information from a manufacturer of the sensor-enabled toothbrush, wherein the set of sensor-enabled device information comprises at least one of: a bristle material, a size of bristles, a length of bristles, a number of bristles, or an angle of bristle cut.

19. The computer program product of claim 18, the computer readable storage device further comprising instructions to analyze the set of toothbrush information in addition to the aggregated usage data.

20. The computer program product of claim 17, the sensor-enabled toothbrush being a medical device, and the condition pertaining to a medical state of the user.

21. The computer program product of claim 17, the computer readable storage device further comprising instructions to determine a medical condition of the user.

22. The computer program product of claim 17, making at least one determination pertaining to at least one of: a level of effectiveness of the toothbrush to treat the condition, and a level of compliance of the user with a set of standards for prevention of a medical condition.

23. The computer program product of claim 17, the network comprising a cloud computing network.

24. The computer program product of claim 17, wherein the characteristic of teeth comprises at least one of: cavities in the teeth, gum recession around the teeth, and hardness of the teeth.

25. A method for deploying a system for analyzing data from a sensor-enabled device, comprising:

providing a computer infrastructure being operable to:

receive a set of usage data, pertaining to a user's use of the toothbrush, from the toothbrush over a cloud network, the set of usage data being collected via at least one sensor integrated with the toothbrush, and the set of usage data comprising: an angle of the toothbrush against at least one tooth of the user, a pressure of the toothbrush against the at least one tooth of the user, a length of time the user brushed the at least one tooth, and an order of brushing of the at least one tooth by the user;

provide a first graph showing average, high, and low pressure applied to each tooth surface;

provide a second graph of an amount of time spent on the each tooth surface;

receive, over the cloud network, usage data pertaining to other users' use of other toothbrushes;

compare the set of usage data, pertaining to the user's use of the toothbrush, to a set of diagnostic information stored in at least one computer storage device, the set of diagnostic information pertaining to a condition treated by use of the toothbrush;

aggregate, into aggregated usage data, a result of the comparison with the usage data pertaining to other users' use of other toothbrushes;

analyze the aggregated usage data;

determine, based on the analysis, a correlation of a characteristic of teeth to a parameter of the toothbrush or use of the toothbrush based on the analyzing;

generate a set of reports based on the comparison, the set of reports indicating at least one recommendation based on the correlation, and the most effective toothpaste and bristle type according to patient phenotype.

\* \* \* \* \*